US00PP24876P3

(12) United States Plant Patent
Wheeler et al.

(10) Patent No.: US PP24,876 P3
(45) Date of Patent: Sep. 16, 2014

(54) BLUEBERRY PLANT NAMED 'BB07-210FL-18'

(50) Latin Name: *Vaccinium corymbosum*
Varietal Denomination: BB07-210FL-18

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 61 days.

(21) Appl. No.: 13/651,214

(22) Filed: Oct. 12, 2012

(65) Prior Publication Data

US 2014/0109264 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB07-210FL-18' as described and shown herein. 'BB07-210FL-18' is a new and distinct low chill tetraploid Southern highbush blueberry (*Vaccinium*) variety of complex ancestry, based largely on *V. corymbosum, V. ashei,* and *V. darrowii,* with a limited contribution from *V. tenellum* and *V. fuscatum.* It is a productive early season ripening variety with high quality fresh market characteristics and is intended for areas which successfully grow lower chill Southern highbush varieties. The flavor is very good with a balance of medium amounts of sweetness and acidity. Berries have a crunchy and juicy texture with medium storage ability of 2 to 3 weeks.

3 Drawing Sheets

BACKGROUND AND SUMMARY

Blueberries are a well-known fruit enjoyed by many throughout the world. One example of an existing, patented blueberry variety is Star, U.S. Plant Pat. No. 10,675. Another example of an existing, patented blueberry variety is Emerald, U.S. Plant Pat. No. 12,165.

Compared to Star, the maturity of the present cultivar, 'BB07-210FL-18', is earlier by 5-7 days; new canes are green color compared to yellowish for Star; and, 'BB07-210FL-18' has a larger berry with rounder shape, more consistent sizing throughout the harvest season, and a slightly sweeter tasting berry.

Compared to Emerald, the maturity of 'BB07-210FL-18' is earlier by 10 days; the bush shape is more upright with a less brushy habit; and the berry has a lighter blue colored, more rounded shape. Also, the harvest season is more concentrated than Emerald.

The present cultivar, 'BB07-210FL-18', provides one or more advantages compared to these and/or other blueberry varieties such as one or more of an early maturity and more easily harvested blueberry.

BRIEF DESCRIPTION OF THE PHOTOGRAPHS

DETAILED DESCRIPTION

Figure 1:
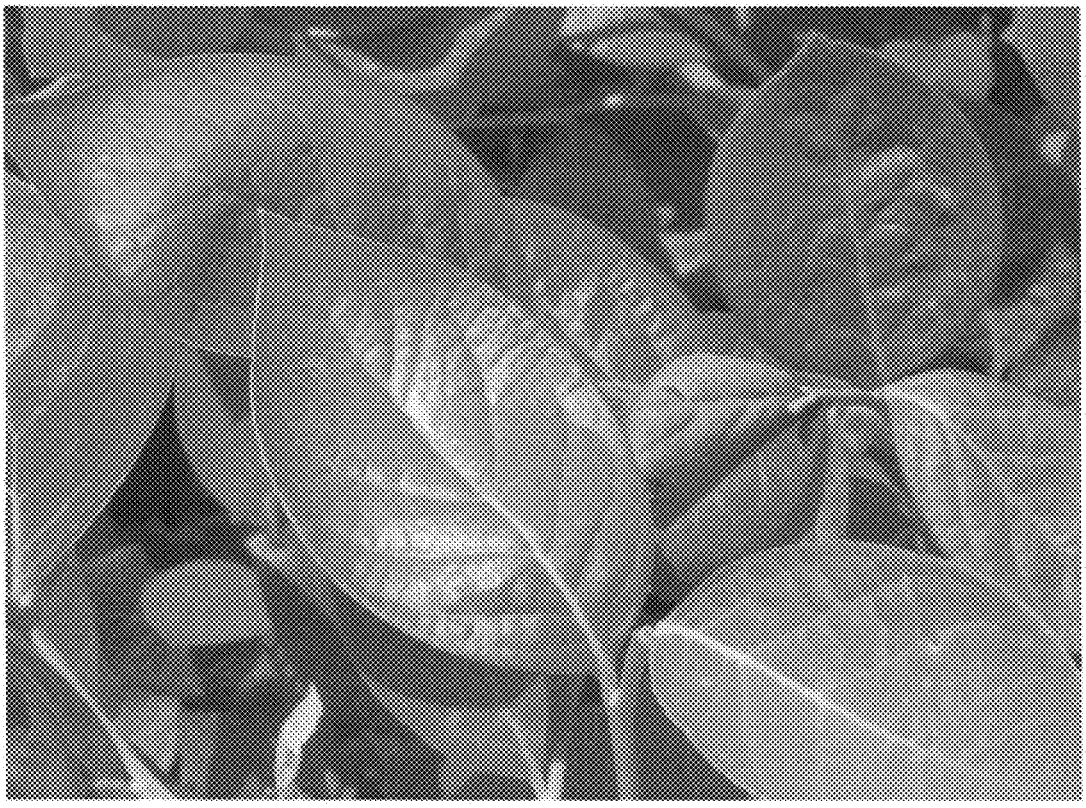
FIG. 1 is a photograph taken in April-May 2012 of the Blueberry cultivar 'BB07-210FL-18', showing mature leaves and their coloration, venation, petioles and slightly visible serration of leaf margin.
Figure 2:
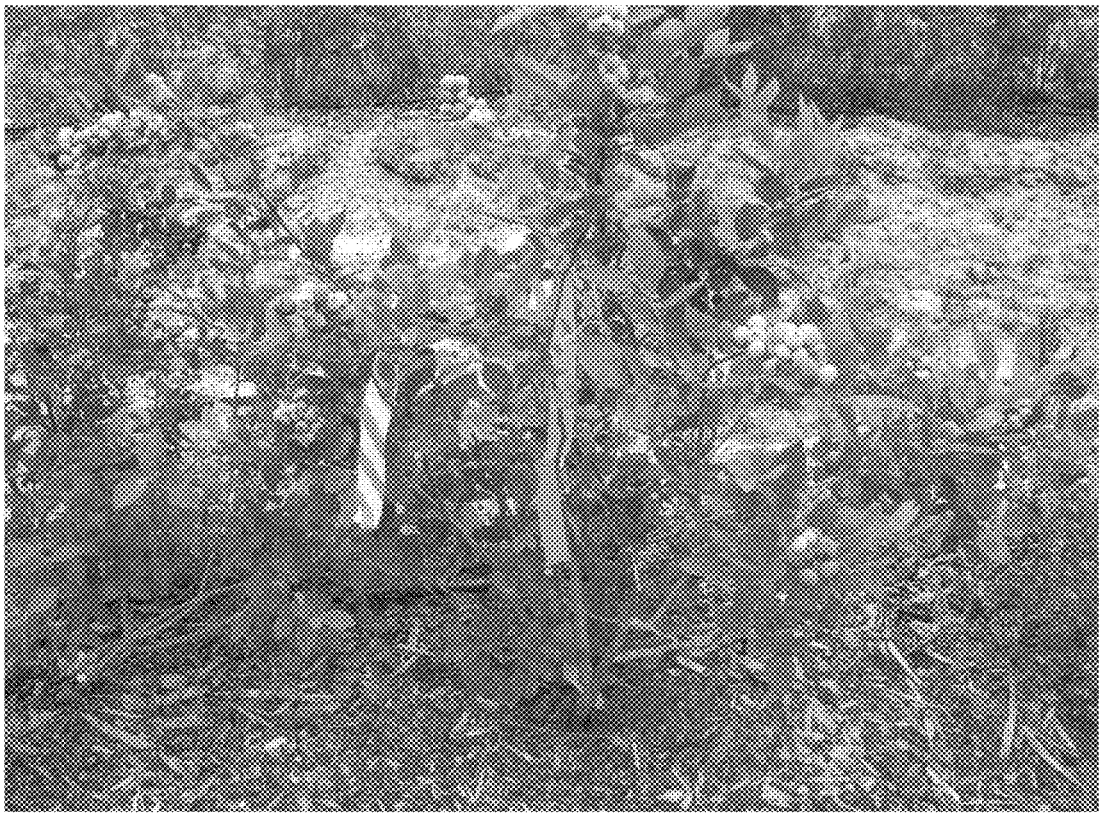
FIG. 2 is a photograph taken in May 2012 of the Blueberry cultivar 'BB07-210FL-18', showing a 4 year old bush at 50% ripened fruit, and also showing the bush shape, branching habit, ripe and unripe fruit size, color and shape, fruit presentation and fruit cluster density.
Figure 3:
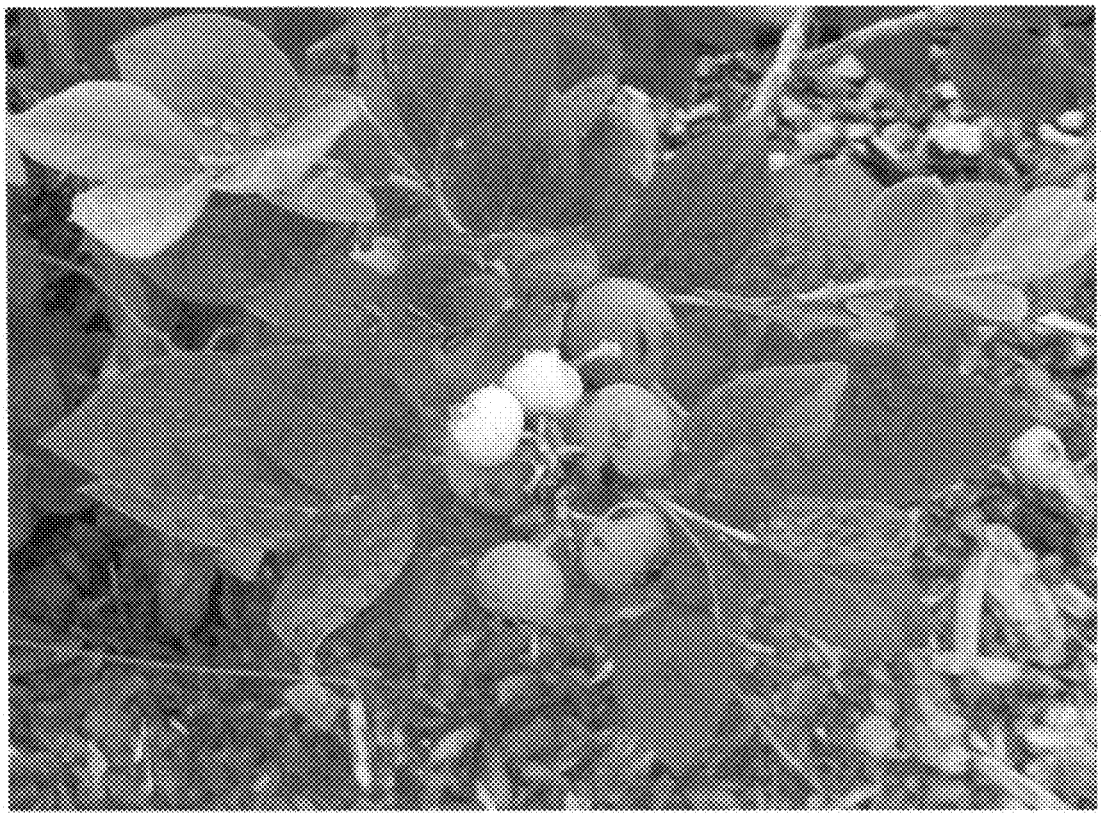
FIG. 3 is a photograph taken in May 2012 of the Blueberry cultivar 'BB07-210FL-18', showing a close-up of a fruit cluster showing ripe and unripe fruit, size, shape, color of fruit, pedicel attachment, cluster density, leaf shape, venation, color.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Interlachen, Fla. Data were obtained on plants that were 5 years old.

Cultivar name: 'BB07-210FL-18'.

Classification:

*Family.*—Ericaceae.

*Botanical name.*—*Vaccinium corymbosum.*

*Common name.*—Blueberry.

Parentage:

*Female parent.*—Name: Springhigh (FL 91-226 unpatented×Southmoon U.S. Plant Pat. No. 9,834). U.S. Plant Pat. No. 16,404. Compared to Springhigh, 'BB07-210FL-18' has a wider leaf width, lighter leaf color, wider corolla opening, and a lighter color of style. 'BB07-210FL-18' averages fewer flowers per cluster, wider and less tall berry shape, different color of ripe berry with and without bloom, more pronounced calyx shape and size. The mean date of first harvest is 10 days later.

*Male parent.*—Name: Springwide (FL83-132 unpatented×Sharpblue unpatented). U.S. Plant Pat. No. 16,333. Compared to Springwide, 'BB07-210FL-18' has a more upright bush shape with fewer mature canes, slightly longer, wider leaf, blooms 10 days earlier, berry harvest more concentrated and mean 50% ripe date is 10 days later, slightly smaller berry, more loose berry cluster.

'BB07-210FL-18' was first asexually propagated by softwood cuttings. For example, softwood cuttings were first taken and rooted in the spring of 2009 in Grand Junction, Mich., and have been propagated several times since in succeeding years. All propagated plants have retained the original characteristics. Softwood cuttings root readily as do microshoots from tissue culture.

All field observations were made in Spring 2012 on a 5-year old individual plant located in a seedling plot near Interlachen, Fla. Laboratory analysis of fruit characteristics were done in Grand Junction, Mich.

General comments: 'BB07-210FL-18' is a new and distinct low chill tetraploid Southern highbush blueberry (*Vaccinium*) variety of complex ancestry, based largely on *V. corymbosum, V. ashei,* and *V. darrowii,* with a limited contribution from *V. tenellum* and *V. fuscatum.* It is a productive early season ripening variety with high quality fresh market characteristics. It is intended for areas which successfully grow lower chill Southern highbush varieties. Winter chilling requirements for successful flowering and leafing are approximately 200-300 hours (<7° C.). Plants of 'BB07-210FL-18' are medium upright with modest growth of primary canes and laterals. Flowering and leafing are synchronous. Flowering is early (northern Florida) and may require frost protection for successful pollination. Plant vigor is very good and does not appear to be overly susceptible to foliar and soil diseases if normal horticultural practices are followed. Its berries are well exposed, very large with a small and dry picking scar, excellent medium blue color with a medium amount of bloom, which is modestly maintained during handling. The flavor is very good with a balance of medium amounts of sweetness and acidity. Berries have a crunchy and juicy texture with medium storage ability of 2 to 3 weeks. Thus, 'BB07-210FL-18' provides an early maturing variety with a concentrated harvest, and very large berry size with excellent eating qualities.

References to color refer to The Pantone Book of Color, Eisemann and Herbert, Harry N. Abrams, Inc. Publishers, New York, ISBN 0-8109-3711-5, 1990.

The Device used to take color readings was a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings—BioWorks FirmTec2, Wamena, Kans.

Average size information:

*General description of 'BB*07-210*FL*-18'.—Medium large bush, medium upright, 5-year plant 144 cm height, 70 cm width, height/width ratio 2:1.

*Growth.*—Very good.

*Productivity.*—Very good.

*Cold hardiness.*—Leaf and flower buds −5° C., open flowers and fruit −2° C.

Specific features of the variety:

Plant:

*Growth habit.*—Medium upright.

*Plant width.*—70 cm at mid-bush.

*Plant height.*—144 cm.

*Spread.*—Canopy 90 cm.

*Productivity.*—4-5 lbs per mature bush.

*Cold hardiness/tolerance.*—Leaf and flower beds −5° C., flowers and fruit −2° C.

*Chilling requirement.*—200-300 hours below 7° C.

*Canes.*—Modestly branched, average 6 canes/bush, 45-60 cm length, medium number of laterals. Mature cane color — Pantone Feather Gray, 15-1305, texture — medium rough.

*Fruiting wood.*—Smooth, immature winter color — Pantone Baked Apple 18-1648; immature summer color — Pantone Tarragon 15-0326; Internode length range 15-20 mm; width 6 mm.

*Surface texture of new wood.*—Smooth.

*Mature canes.*—Circular, width 22 mm.

*Time of beginning of leaf bud burst* (*include location*(*s*)).—February 2 (Interlachen, Fla.).

*Time of beginning of flowering* (*include location*(*s*)).—January 25 (Interlachen, Fla.).

*Time of fruit ripening* (*include location*(*s*)).—April 15 (Interlachen, Fla.).

*Disease resistance/susceptibility.*—None known.

Foliage:

*Leaf color.*—Upper — Pantone Chive 19-0323, Lower — Pantone Peridot 17-0336.

*Leaf arrangement.*—Alternate.

*Shape.*—Elliptic.

*Leaf margins.*—Slightly serrated.

*Leaf venation.*—Pinnate.

*Leaf apices.*—Acuminate.

*Leaf bases.*—Cuneate.

*Vein and petiole colouration.*—Pantone Herbal Garden 15-0336.

*Petiole length.*—3 mm.

*Leaf dimensions.*—Overall shape: 70 mm-82 mm, average 74 mm. Width: 46 mm-53 mm, average 51 mm.

*Leaf margins.*—Slightly serrated; no pubescence or nectaries.

*Leaf surface.*—Smooth upper and lower, no pubescence.

Flower:

*Flower shape.*—Urceolate.

*Flower bud number.*—Medium high.

*Flowers per cluster.*—6-7.

*Flower fragrance.*—Lightly floral.

*Corolla color.*—Pantone Chalk 12-2902.

*Corolla length.*—8 mm.

*Corolla aperture width.*—7 mm.
*Flower peduncle.*—Length 11 mm.
*Color.*—Pantone Herbal Garden 15-0336.
*Flower pedicel.*—3 mm.
*Color.*—Pantone Willow 16-0632.
*Calyx* (*with sepals*).—2 mm.
*Color.*—Pantone Willow 16-0632.
*Stamen.*—Length: 6-7 mm.
*Number per flower.*—10.
*Filament color.*—Pantone Peach Bloom 15-1327.
*Style.*—8 mm from top of ovary to stigma tip.
*Color.*—Pantone Straw 13-0922.
*Pistil.*—8 mm.
*Ovary color.*—NA.
*Anther.*—Length: 4 mm.
*Number.*—10/flower.
*Color.*—Pantone Peach Bloom 15-1327.

Pollen:
*Abundance.*—Medium high.
*Color.*—Pantone Golden Cream 13-0939.

Fruit:
*Date of* 50% *maturity.*—April 15 (Interlachen, Fla.).
*Yield.*—4-5 lbs/bush.
*Berry color.*—With wax: Pantone Purple Cloud 16-3919, SpectraMagic (L,a,b) 40.25, 1.69, −1.97. With wax removed: Pantone Purple Velvet 19-3725.
*Berry flesh color.*—Pantone Frozen Dew 13-0513.
*Berry surface wax abundance.*—Medium, moderately persistent.
*Calyx.*—Width — 7 mm; depth — 2 mm; shape — 5 lobed with pronounced ridges.
*Berry weight.*—2.5 grams/berry.
*Berry size diameter.*—20 mm width, 12 mm height, Aspect (H/W) — 0.7.
*Berry shape.*—Oblate.
*Fruit stem scar.*—Medium small, dry, 2 mm.
*Cluster density.*—Medium loose.
*Detachment force.*—Medium.
*Self-fruitfulness.*—Poor, will need cross pollination for maximum yield and size.
*Berry firmness.*—Very firm, FirmTec 2 score — 242 g/mm$^2$.
*Berry sweetness.*—Medium, Brix ° 9.2.
*Berry acidity.*—Medium: TA — 0.63.
*Berry flavor and texture.*—Very good and balanced, juicy and crunchy texture.
*Suitability for mechanical harvesting.*—Bush shape, berry firmness, and detachment appear good for mechanical harvesting.

Seed:
*Seed abundance in fruit.*—Medium (10-25 seeds/fruit).
*Seed color.*—Pantone Baked Clay 18-1441.
*Seed dry weight.*—NA.
*Seed size.*—Medium, 1-1.5 mm/seed.

Possible typical market uses: Fresh market, processing into jams, puree, yogurt.

Storage quality: Medium, 2-3 weeks in refrigerated storage.

What is claimed is:

1. A new and distinct cultivar of Blueberry plant named 'BB07-210FL-18' as described and shown herein.

* * * * *